(12) United States Patent
Ohara et al.

(10) Patent No.: US 6,488,632 B2
(45) Date of Patent: Dec. 3, 2002

(54) ULTRASONIC ENDOSCOPE

(75) Inventors: Kenichi Ohara, Gunma; Toshiyuki Hashiyama, Saitama, both of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/987,314

(22) Filed: Nov. 14, 2001

(65) Prior Publication Data

US 2002/0062084 A1 May 23, 2002

(30) Foreign Application Priority Data

Nov. 21, 2000 (JP) ........................................ 2000-353745

(51) Int. Cl.[7] ................................................ A61B 8/00
(52) U.S. Cl. ...................... 600/462; 600/459; 600/466
(58) Field of Search ................................ 600/459, 463; 29/25.35

(56) References Cited

U.S. PATENT DOCUMENTS 5,044,053 A * 9/1991 Kopel et al. ................ 29/25.35
5,876,345 A * 3/1999 Eaton et al. ................. 600/463
5,947,905 A * 9/1999 Hadjicostis et al. ........ 600/463
6,228,032 B1 * 5/2001 Eaton et al. ................. 600/463

* cited by examiner

Primary Examiner—Marvin M. Lateef
Assistant Examiner—Ruby Jain
(74) Attorney, Agent, or Firm—Greenblum & Bernstein, P.L.C.

(57) ABSTRACT

An ultrasonic endoscope has a bending portion, an ultrasonic probe, and a flexible circuit board. The bending portion, connected to the point of a flexible tube, bends by remote control. The ultrasonic probe has a plurality of ultrasonic wave vibrators, which are arranged circumferentially, and send ultrasonic waves radially and receive echoes of the ultrasonic waves. The flexible circuit board, which transmits signals associated with the ultrasonic waves and the echoes, is constructed of a plurality of flexible circuit board strips in the bending portion so as to allow a bending motion. The plurality of ultrasonic wave coaxial lines, which are provided in the flexible tube to form an ultrasonic wave coaxial cable and are connected to the plurality of flexible circuit board strips, are loose and flexible in a given range.

3 Claims, 10 Drawing Sheets

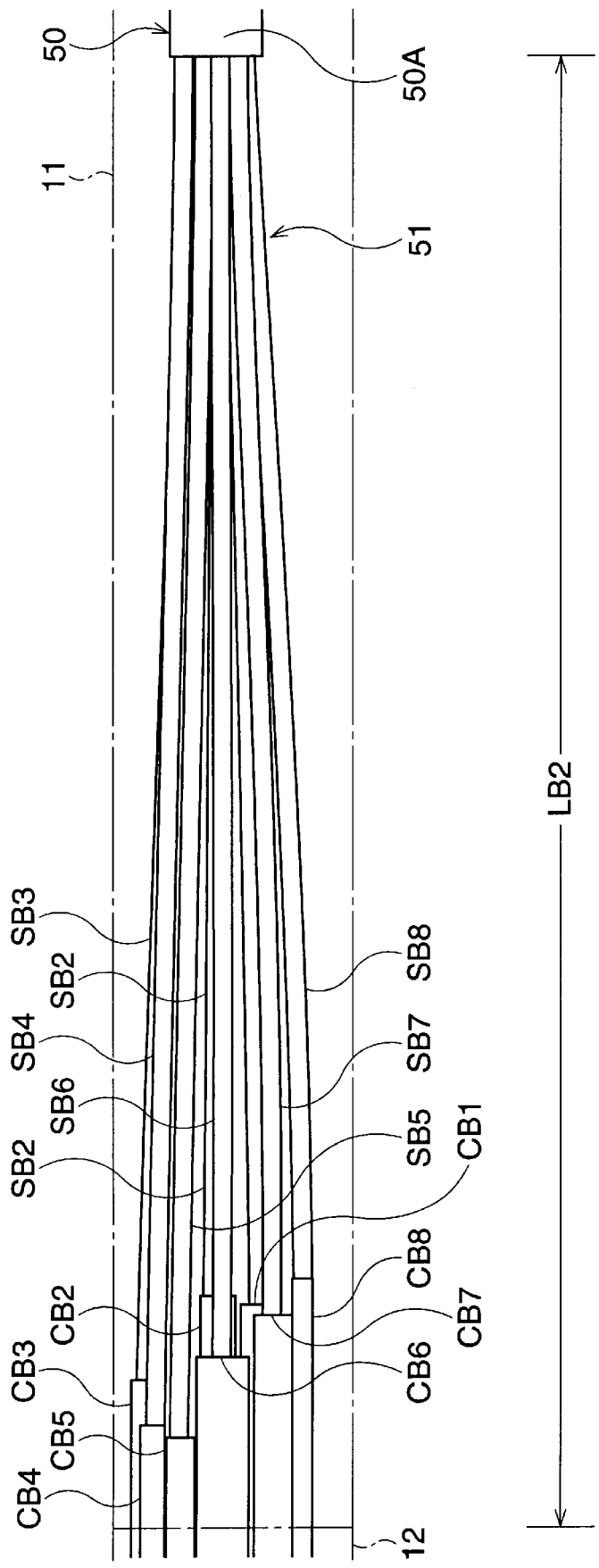

ULTRASONIC ENDOSCOPE

BACKGROUND OF THE INVENTION

1. Field of the Invention

The present invention relates to an ultrasonic endoscope, which uses ultrasonic waves for the diagnosis of a diseased tissue. Especially, the present invention relates to a construction of the portion of the point in the endoscope.

2. Description of the Related Art

In the ultrasonic endoscope, an ultrasonic probe having ultrasonic wave vibrators is provided at the distal end of the endoscope. The ultrasonic probe sends ultrasonic waves and receives echoes of the sent ultrasonic waves.

For the scanning method, a radial scanning or a linear scanning is used. For example, when diagnosing an organ (body-cavity), into which the ultrasonic endoscope cannot be inserted, the radial scanning is performed. The endoscope is inserted toward an organ adjacent to the observed organ, ultrasonic waves are sent radially from the ultrasonic probe. Conventionally, a mechanical-type radial scanning is applied, where a series of ultrasonic wave vibrators is aligned along an axis of the probe and revolves on the axis to send the ultrasonic waves radially.

However, in the case of the mechanical type radial scanning, a color-image, partially colored by Red (R), G (Green), B(Blue), which is effective for diagnosis of the diseased areas, cannot be displayed on the monitor.

Further, while manipulating the bending portion, various forces act on signal transmitting members for transmitting signals associated with the ultrasonic waves and the echoes. Therefore, a greater durability for the bending motion is required for the signal transmitting members provided in the distal end of the endoscope.

SUMMARY OF THE INVENTION

Therefore, an object of the present invention is to provide an ultrasonic endoscope that is capable of obtaining an observed-image for diagnosis, and further that is durable in its bending motion.

An ultrasonic endoscope according to the present invention is an endoscope for performing electronic radial scanning. A bending portion formed in a tube is connected to the point of a flexible tube, which is inserted in a body, or organ. The flexible tube is normally connected to a manipulator portion of the endoscope, and an operator, such as a doctor, bends the bending portion by manipulating a manipulating knob, which is operatively connected to the bending portion. Namely, the bending portion bends by remote control.

An ultrasonic probe for the electronic radial scanning is operatively connected to the bending portion. For example, a solid point-base portion is connected to the bending portion and the ultrasonic endoscope is attached to the point-base portion.

The ultrasonic probe has a plurality of ultrasonic wave vibrators, which are arranged circumferentially to perform the electronic radial scanning. The plurality of ultrasonic wave vibrators send ultrasonic waves radially around a center axis of the ultrasonic probe and receive echoes of the ultrasonic waves.

According to the present invention, a flexible circuit board is provided in the endoscope. The flexible circuit board transmits signals associated with ultrasonic waves and echoes, so that an ultrasonic-image, representing a section-image in the body, is obtained at the ultrasonic wave diagnosis apparatus. As electronic scanning (not mechanical scanning) is performed, an ultrasonic color-image is obtained as required by simultaneously sending multiple ultrasonic waves, each frequency of which is different, or an ultrasonic pulse-width image is obtained by coloring in accordance with contrast of the echoes. These images cannot be obtained by mechanical radial scanning.

In the bending portion, the flexible circuit board is constructed of a plurality of flexible circuit board strips so as to allow a bending motion, namely, to be capable of withstanding the bending motion. The plurality of flexible circuit board strips extends along a central axis of the bending portion (herein, represented by "a first central axis"). The signal-transmitting member in the bending portion is composed of a plurality of flexible circuit board strips, which prevent snapping while the bending portion is manipulated. The plurality of flexible circuit board strips enables the circumferential arrangement of the ultrasonic wave vibrators, namely, the electronic radial scanning. Note that, the width of each flexible circuit board strips is defined in accordance with a radius of the bending portion.

An ultrasonic wave coaxial cable, which is provided in the flexible tube and which transmits the signals associated with the ultrasonic waves and echoes, is formed by bundling a plurality of ultrasonic wave coaxial signal lines. Part of the ultrasonic wave coaxial signal lines are separate and extend from the ultrasonic wave coaxial cable along a central axis of the flexible tube (herein, represented by "a second central axis"). The plurality of ultrasonic wave coaxial signal lines are connected to the plurality of flexible circuit board strips so that the signals associated with the ultrasonic wave and the echoes are transmitted between the ultrasonic wave diagnosis apparatus and the ultrasonic probe.

The plurality of ultrasonic wave coaxial signal lines are flexible and loose in a given range so as to "accept", or absorb the compressing and extending forces. Note that, the forces operate along the first and second central axes, against the plurality of flexible circuit board strips, the plurality of ultrasonic wave coaxial signal lines, and the ultrasonic wave coaxial cable. While the bending portion is manipulated, the loose coaxial signal lines are flexed and pulled more compared to the flexible circuit board strips when the compressing and expanding forces occur along the first and second central axes. Namely, the unbundled coaxial lines absorb the compressing and extending forces by flexure and extending. Thus, excessive flex and extension do not occur in the circuit board strips while bending the bending portion so that snapping of the printed wiring on the circuit board strips does not occur.

To provide sufficient flexibility for the ultrasonic wave coaxial signal lines, preferably, the length of the given range along the second axis is equal to or more than the length of the plurality of flexible circuit board strips along the first central axis.

As for the total construction of the flexible circuit board, the flexible circuit board strips may be composed of the flexible circuit board strips (pieces), which are connected to the ultrasonic wave vibrators separately. However, to make the flexible circuit board strips stronger than the ultrasonic wave coaxial signal lines with respect to the compressing and expanding forces, preferably, the flexible circuit board is formed by partially cutting a single rectangular flexible circuit board such that the plurality of flexible circuit board strips are formed and then rounding said cut rectangular flexible circuit board so as to form a cylindrical shape.

BRIEF DESCRIPTION OF THE DRAWINGS

The present invention will be better understood from the description of the preferred embodiment of the invention set fourth below together with the accompanying drawings, in which:

FIG. 10 is a schematic view of ultrasonic wave coaxial signal lines and an ultrasonic wave coaxial cable in the flexible tube.

DESCRIPTION OF THE PREFERRED EMBODIMENTS

Hereinafter, the preferred embodiment of the present invention is described with reference to the attached drawings.

Figure 1:
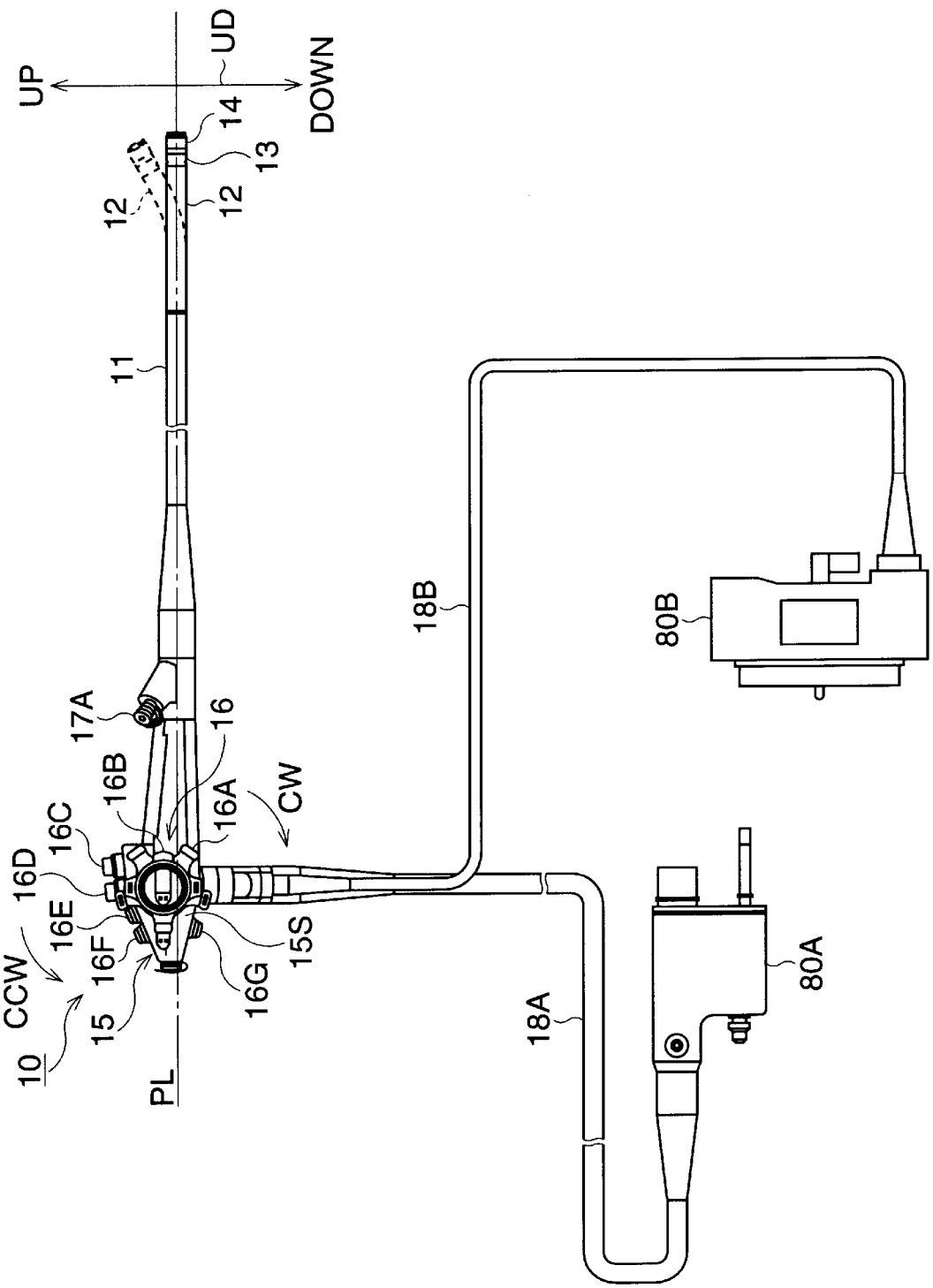
FIG. 1 is a side view of an ultrasonic endoscope of a first embodiment.
Figure 2:
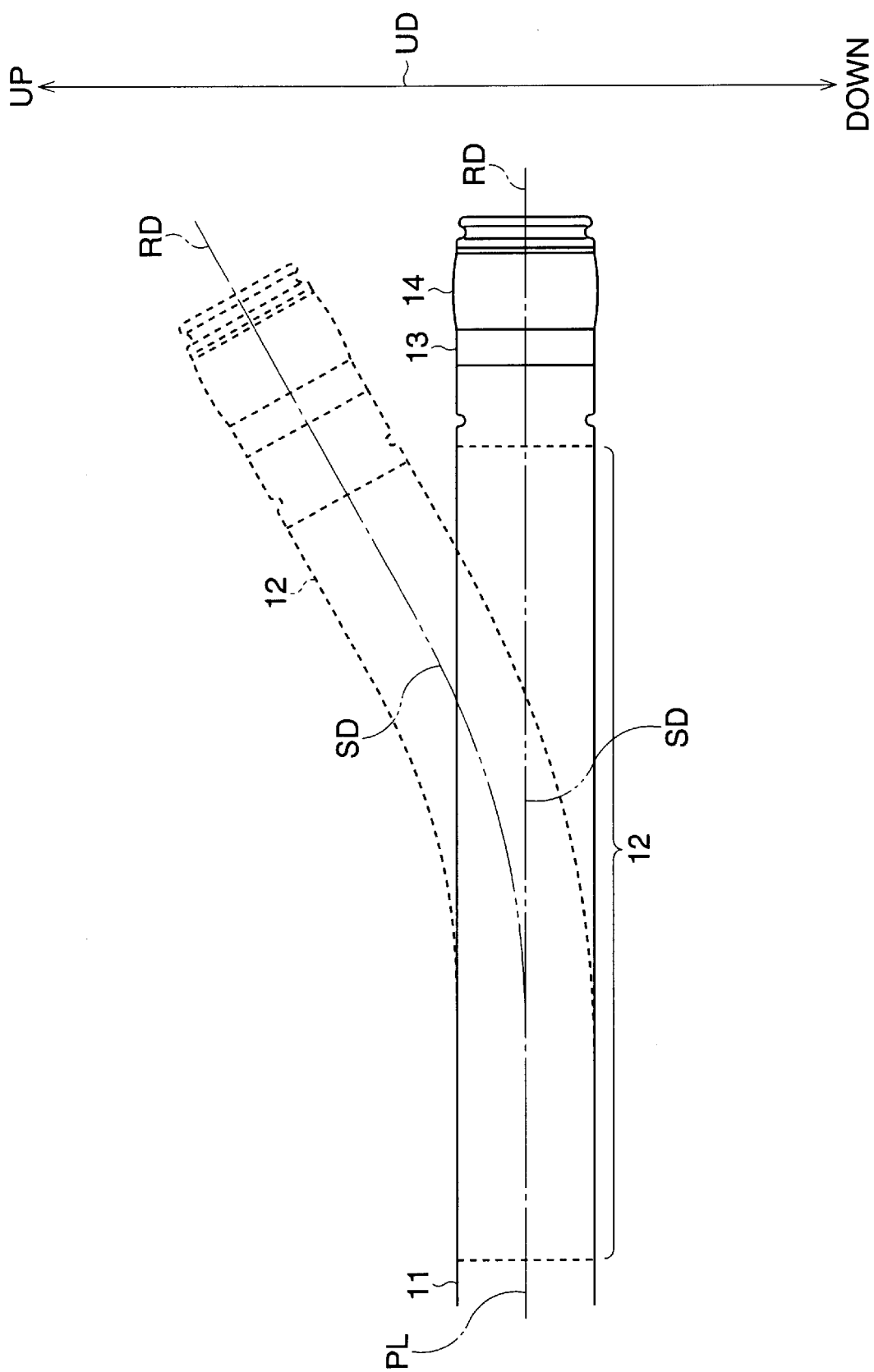
FIG. 2 is a view showing a portion of the point of the ultrasonic endoscope.

FIG. 1 is a side view of an ultrasonic endoscope of the first embodiment. FIG. 2 is a view showing a portion of the point of the ultrasonic endoscope.

An ultrasonic endoscope 10 has a flexible tube 11, manipulator portion 15, first and second connected tubes 18A and 18B, and first and second connecters 80A and 80B. A bending portion 12, a point-base portion 13 and an ultrasonic probe 14 are provided at the distal end of the flexible tube 11, namely, the distal end of the endoscope 10.

The bending portion 12 is connected to the point of the flexible tube 11, the point-base portion 13 is attached to the bending portion 12, and the ultrasonic probe 14 is attached to the point-base portion 13. The first and second connecters 80A and 80B are connected to the first and second connected tubes 18A and 18B respectively, and the first and second connected tubes 18A and 18B are connected to the manipulator portion 15. The flexible tube 11, which is inserted into a given organ (body-cavity), is connected to the manipulator portion 15.

When performing the diagnosis, the first connecter 80A is connected to a video-processor (not shown) having a light source and signal processor circuits, the second connecter 80B is connected to an ultrasonic wave diagnosis apparatus (not shown), and then the flexible tube 11 is inserted into the body-cavity. A first monitor for displaying the observed color image (not shown) is connected to the video-processor and a second monitor for displaying an ultrasonic-image (not shown) is connected to the ultrasonic wave diagnosis apparatus. An operator, such as a doctor, operates a set of manipulating knobs 16, which are composed of an up-down knob 16A and a left-right knob 16B and are provided on the manipulator portion 15, with his right hand. Then, the operator holds the flexible tube 11 in his left hand and inserts the flexible tube 11 toward observed-organ in a patient's body.

A pair of fiber-optic bundles (herein not shown) are provided between the first connector 80A and the ultrasonic probe 14, light radiated from the light source in the video-processor passes through the fiber-optic bundles and is emitted from the distal end of the fiber-optic bundles, namely, the distal end of the ultrasonic endoscope 10. Consequently, an observed-object is illuminated by the light emitted from the fiber-optic bundles.

The ultrasonic endoscope 10 functions as a video-scope. Namely, an objective lens (herein not shown) and an image sensor (not shown), such as a CCD (Charge-Coupled Device), are provided in the ultrasonic probe 14, and an image signal cable (herein not shown) connecting the image sensor and the video-processor is provided in the ultrasonic endoscope 10. The light reflected on the object portion passes trough the objective lens and reaches the image sensor. Thus, the object image is formed on the image sensor and image signals corresponding to the object image are generated. The image signals are read from the image sensor and fed to the video-processor. In the video-processor, various processes are performed on the image signals, so that video signals, such as an NTSC signal, are generated. The video signals are output to the first monitor so that the object image is displayed on the first monitor.

The bending portion 12 is bent by the operator's remote control, namely, by manipulating the up-down knob 16A and/or the left-right knob 16B. The up-down knob 16A and the left-right knob 16B, provided on the right side surface 15S of the manipulator portion 15, are both rotatable dial type knobs and are connected to the bending portion via wires (herein not shown). The bending portion 12 bends along the two bending directions, namely, the up-down direction shown by "UD" and the left-right direction, by turning the up-down knob 16A and the left-right knob 16B.

When extending the flexible tube 11 so that it is straight and untwisted, the central axis "PL" of the flexible tube 11 becomes a straight-line and the manipulator portion 15 is formed along a central axis "PL" of the flexible tube 11. While the bending portion 12 is in a neutral posture, the bending portion 12 extends along the central axis PL. Therefore, when defining the central axis "SD" of bending portion 12 and the central axis of the point "RD" of the solid point-base portion 13 and the solid ultrasonic probe 14, the central axis SD and the central axis of the point RD coincide with the central axis PL, as shown in FIG. 2.

When the operator turns the up-down knob 16A counter-clockwise (shown by "CCW"), the bending portion 12 bends toward the up direction, as shown by the broken line in FIG. 2. Namely, the ultrasonic probe 14 has a given angle to the central axis PL. When the operator turns the up-down knob 16A clockwise (shown by "CW"), the bending portion 12 bends toward the down direction. Similarly, the bending portion 12 bends to the left and right direction by turning the left-right knob 16B counterclockwise or clockwise respectively.

When inserting the flexible tube 11, the operator manipulates the distal end of the endoscope 10 and the flexible tube 11 while watching the color image displayed on the first monitor. Speaking correctly, the operator "shakes" the manipulator portion 15 while holding the manipulating knobs 16 such that the flexible tube 11 turns, or revolves around the central axis PL.

When the ultrasonic probe 14 reaches objective portion, ultrasonic wave pulse signals are output from the ultrasonic wave diagnosis apparatus and are fed to the ultrasonic probe 14 via the second connecter 80B. The ultrasonic probe 14 sends ultrasonic waves on the basis of the ultrasonic wave pulse signals and then receives the echoes of the ultrasonic waves. The echoes are transferred to pulse signals and then the pulse signals are fed to the ultrasonic wave diagnosis apparatus via the second connecter 80B. In the ultrasonic wave diagnosis apparatus, various processes are performed on the input pulse signals corresponding to the echoes, so that an ultrasonic-image, which is a section image along the sending direction of the ultrasonic waves, is displayed on the second monitor.

A forceps tube (herein not shown) is provided between the manipulator portion 15 and the ultrasonic probe 14. A given forceps for treating the diseased portion is inserted from a forceps entrance 17A. Further, a pair of delivery tubes (herein not shown) for supplying water to the point-base portion 13 is provided in the ultrasonic endoscope 10. At the manipulator portion 15, a delivery switch button 16C is provided. When the delivery switch button 16C is operated, the water flows in the delivery tubes and is emitted from the side surface of the point-base portion 13. An absorption switch button 16D, a freeze switch button 16E, a copy switch button 16F, and a recording switch button 16G are provided on the manipulator portion 15. These switches 16C, 16D, 16E, 16F, and 16G are arranged along the up-down direction UD.

Figure 3:
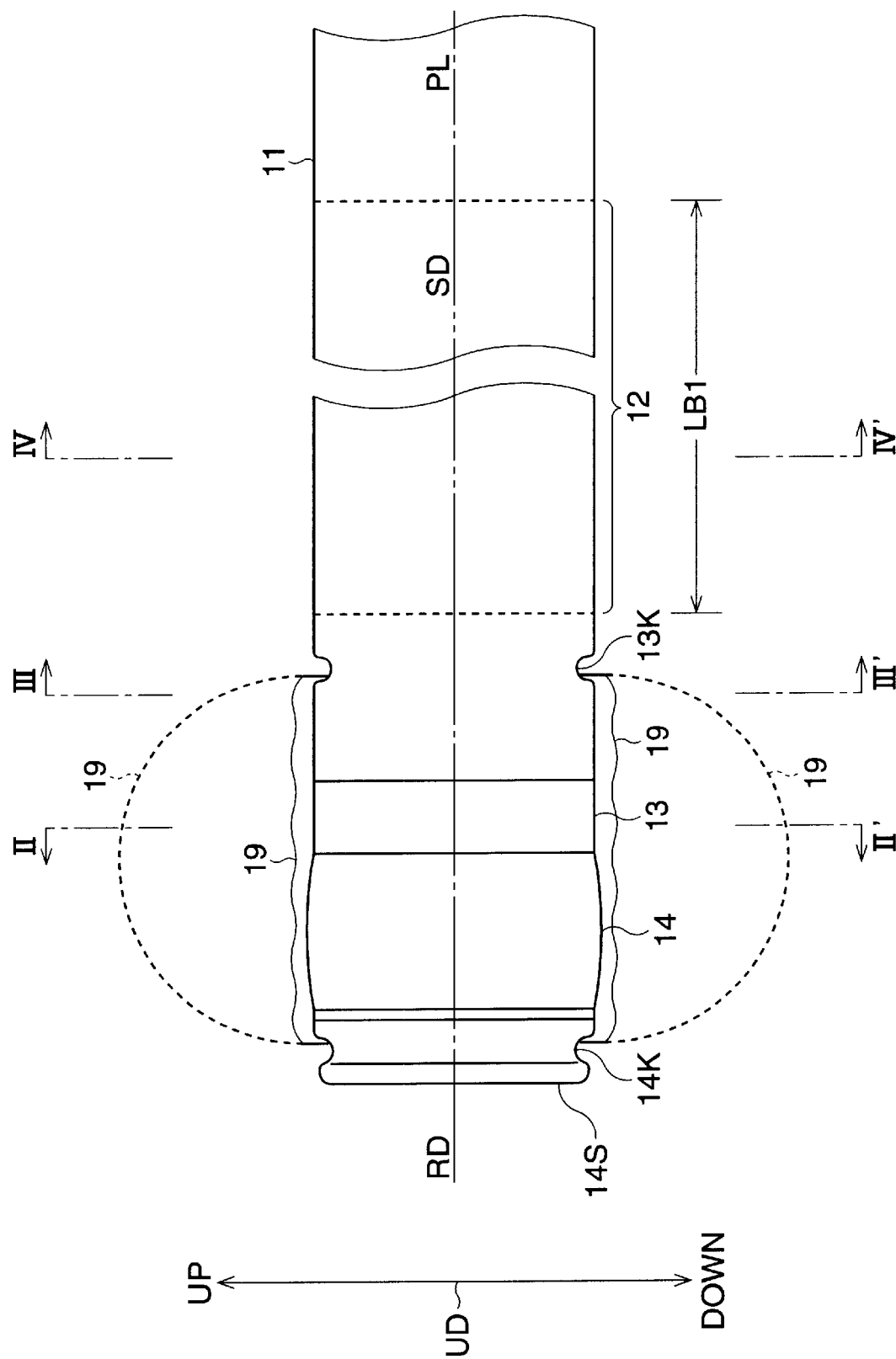
FIG. 3 is a side view showing the point-base portion and the ultrasonic probe, seen from the left side.
Figure 4:
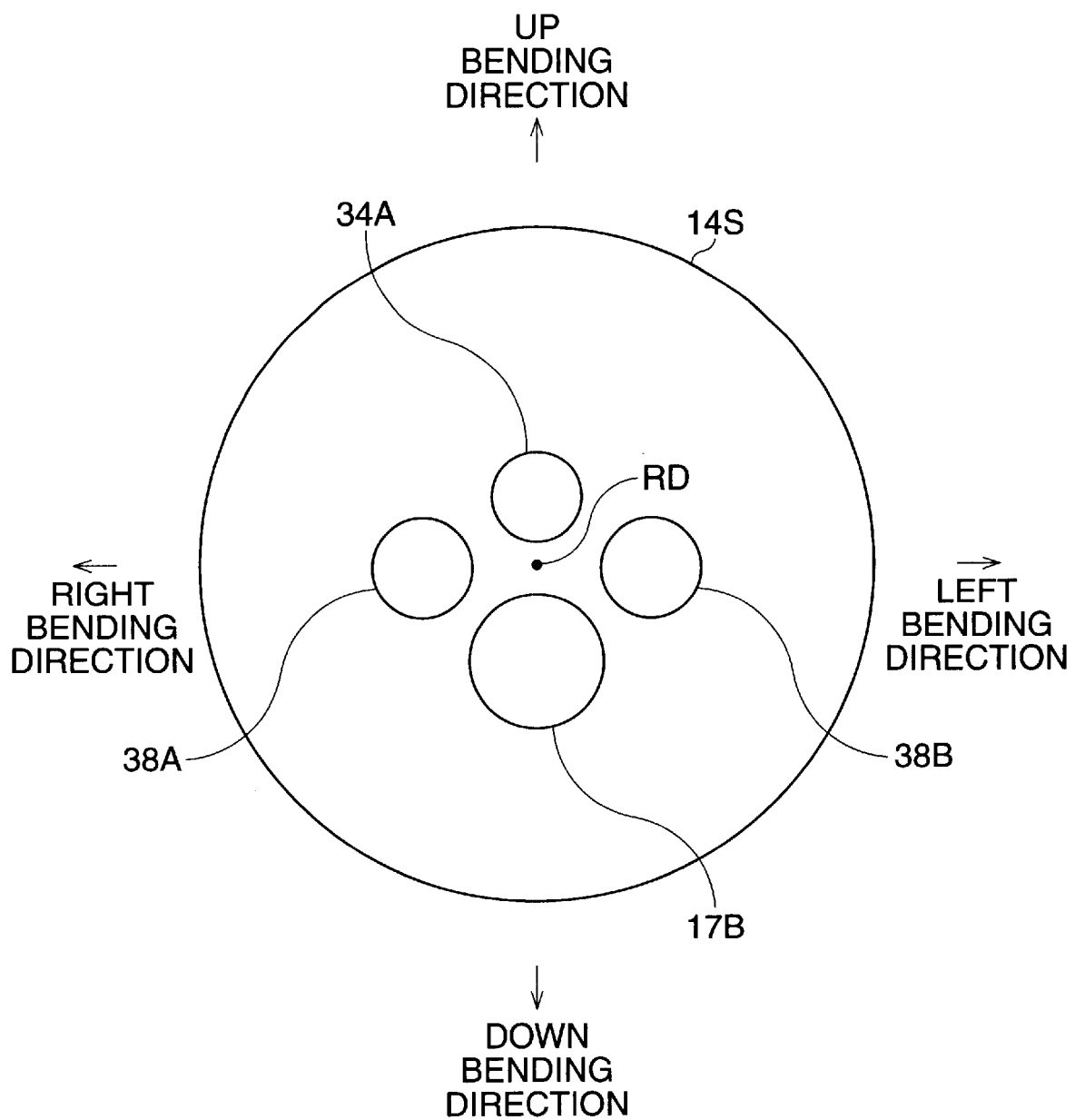
FIG. 4 is a front view of the ultrasonic probe.

FIG. 3 is a side view showing the point-base portion 13 and the ultrasonic probe 14, seen from the left side. FIG. 4 is a front view of the ultrasonic probe 14.

The stiff point-base portion 13 and the ultrasonic probe 14 are covered with a balloon 19 when performing the ultrasonic wave diagnosis. To fix the balloon 19, a first groove 14K is formed around the outer surface of the ultrasonic probe 14 and a second groove 13K is formed around the outer surface of the point-base portion 13. The water, flowing through the delivery tubes, comes out of two outlets (not shown) on the outer surface of the point-base portion 13. To obtain a precise ultrasonic image, the water in a tank (not shown) provided at the video-processor is supplied inside the balloon 19 via the couple of delivery tubes, so that the balloon 19 expands, as shown by the broken line. After the diagnosis, the water in the balloon 19 is absorbed by pushing the absorption switch button 16E and is then fed to an absorbing unit (not shown) via the couple of delivery tubes.

As shown in FIG. 4, on the front surface 14S of the ultrasonic probe 14, an objective lens 34A is provided, and emitting surfaces 38A and 38B of the fiber-optic bundles and a forceps outlet 17B of the forceps tube are formed. The light, reflected on the subject, passes through the objective lens 34A and reaches the image sensor within the ultrasonic probe 14. The objective lens 34 is provided on the front surface 14S, namely, the point surface of the ultrasonic probe 14 (not side surface). Therefore, the visual field broads along the central axis RD of the point. As the visual field substantially coincides with the direction of progress of the distal end of the endoscope 10, the operator can insert the flexible tube 11 and manipulate the manipulator portion 15 while looking at the progress of the probe 14.

Figure 5:
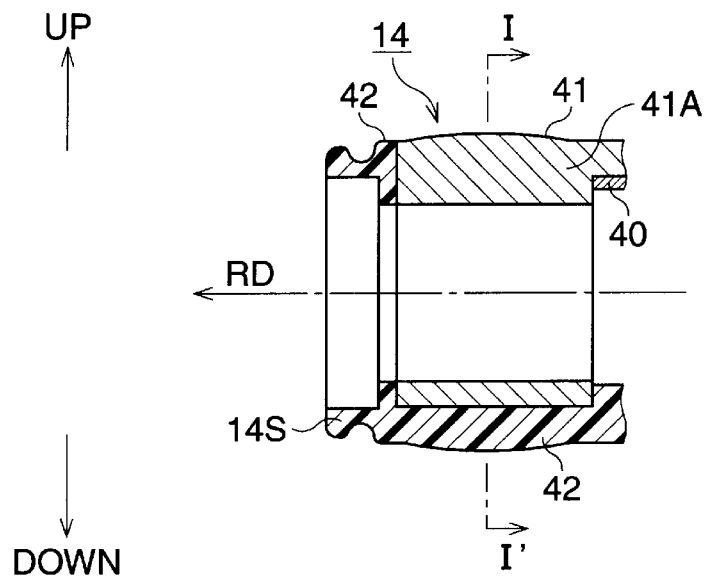
FIG. 5 is a schematic section view of the ultrasonic probe from the side, passing through the center axis of the point and along the up-down direction.
Figure 6:
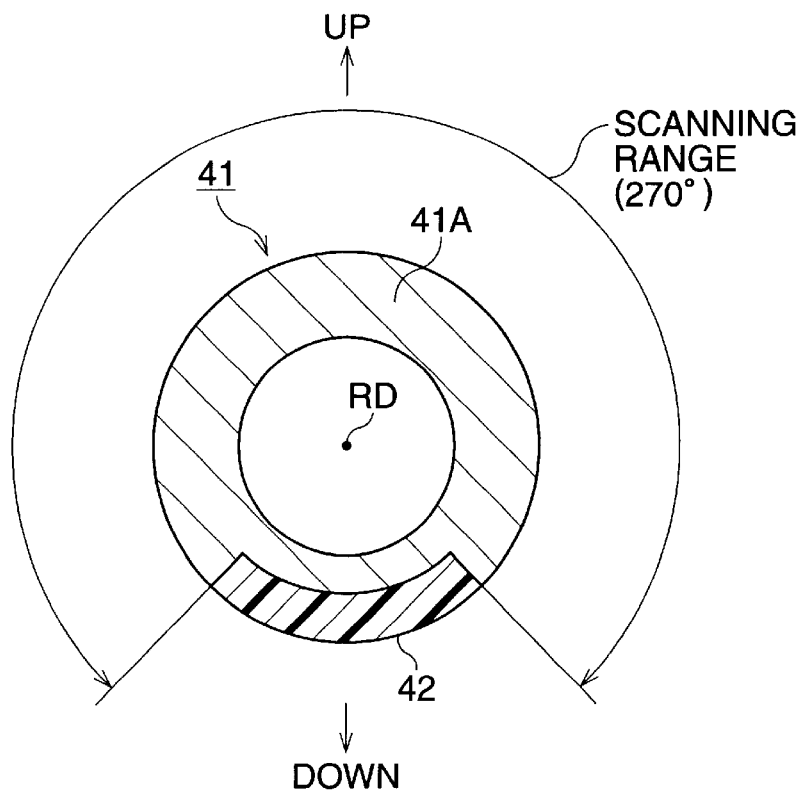
FIG. 6 is a schematic section view of the ultrasonic probe at line I–I' shown in FIG. 5, seen from the front.

FIG. 5 is a schematic section view of the ultrasonic probe 14, passing through the central axis of the point RD and along the up-down direction UD. FIG. 6 is a schematic section view of the ultrasonic probe 14 across the line I–I' shown in FIG. 5, seen from the front surface 14S. Note that, the fiber-optic bundles, forceps tubes, and the image signal cable connected to the image sensor are not shown in FIGS. 5 and 6.

The ultrasonic probe 14 includes an ultrasonic wave sender-receiver 41 and a supporting member 42. The ultrasonic wave sender-receiver 41 is formed along the circumference of the cylindrical ultrasonic probe 14, and the supporting member 42 supports the ultrasonic wave sender-receiver 41. A flexible circuit board 40 for transmitting signals associated with the ultrasonic waves and their echoes is connected to the ultrasonic wave sender-receiver 41. The ultrasonic wave sender-receiver 41 is composed of a plurality of ultrasonic wave vibrators 41A, which are arranged along the circumference of the ultrasonic probe 14 to perform the radial scanning. In this embodiment, each of the plurality of ultrasonic wave vibrators 41A is a piezoelectric element, which transfers electric signals to mechanical vibration and vice versa.

High frequency pulse signals, input to the ultrasonic wave sender-receiver 41 via the flexible circuit board 40, are transformed to ultrasonic waves by the piezoelectric effect. The ultrasonic wave sender-receiver 41 radially sends the ultrasonic waves around the central axis of the point RD, in order. Each of the ultrasonic waves is sent in accordance with a predetermined frequency and timing to perform the electronic radial scanning. In this embodiment, the scanning range is 270 degrees. When the ultrasonic wave sender-receiver 41 receives the echoes in order, the echoes are transformed to given electric signals by the inverse piezoelectric effect. The electric signals are fed to the ultrasonic wave diagnosis apparatus via the flexible circuit board 40.

Figure 7:
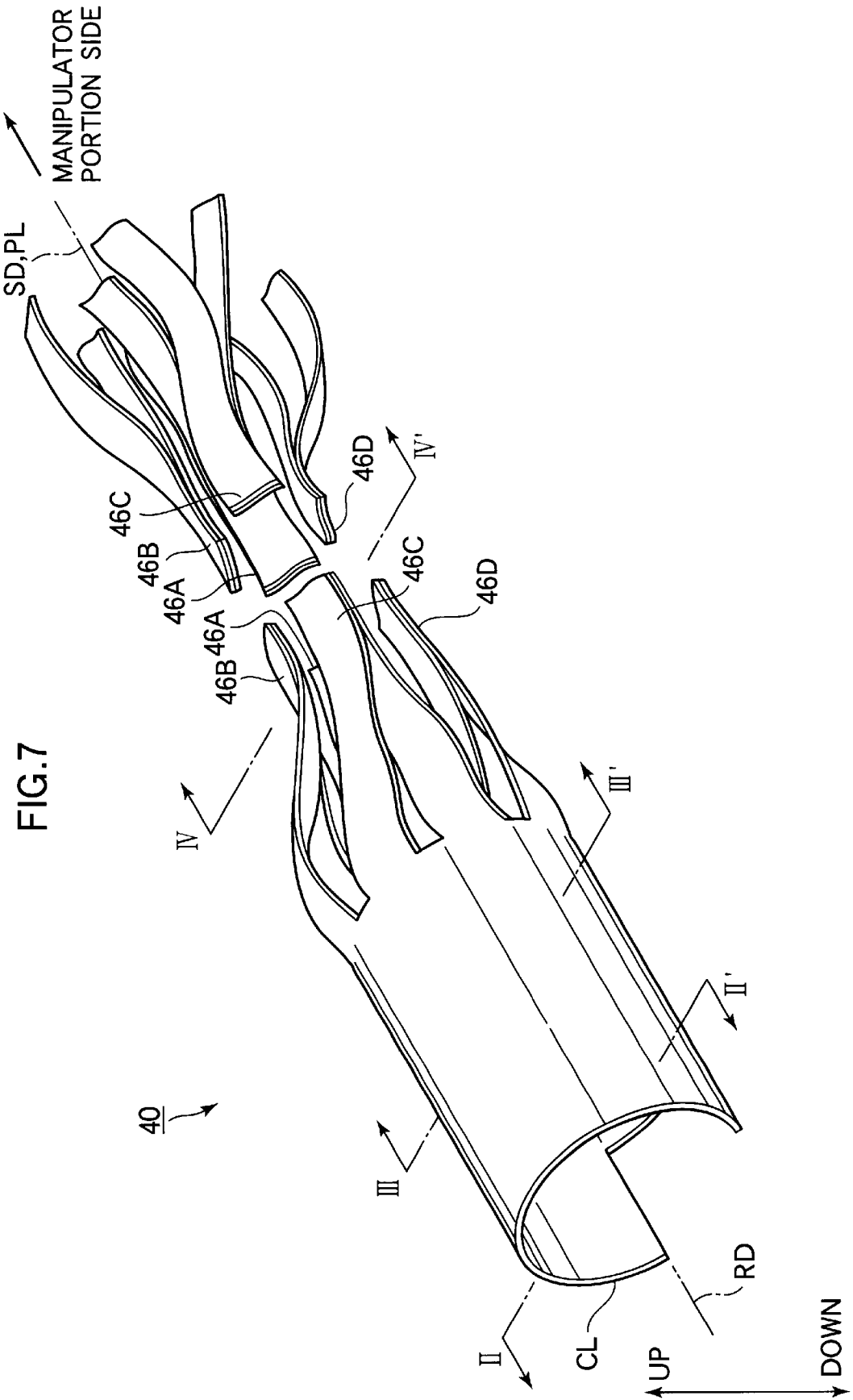
FIG. 7 is a schematic perspective view of the flexible circuit board formed in the endoscope.
Figure 8:
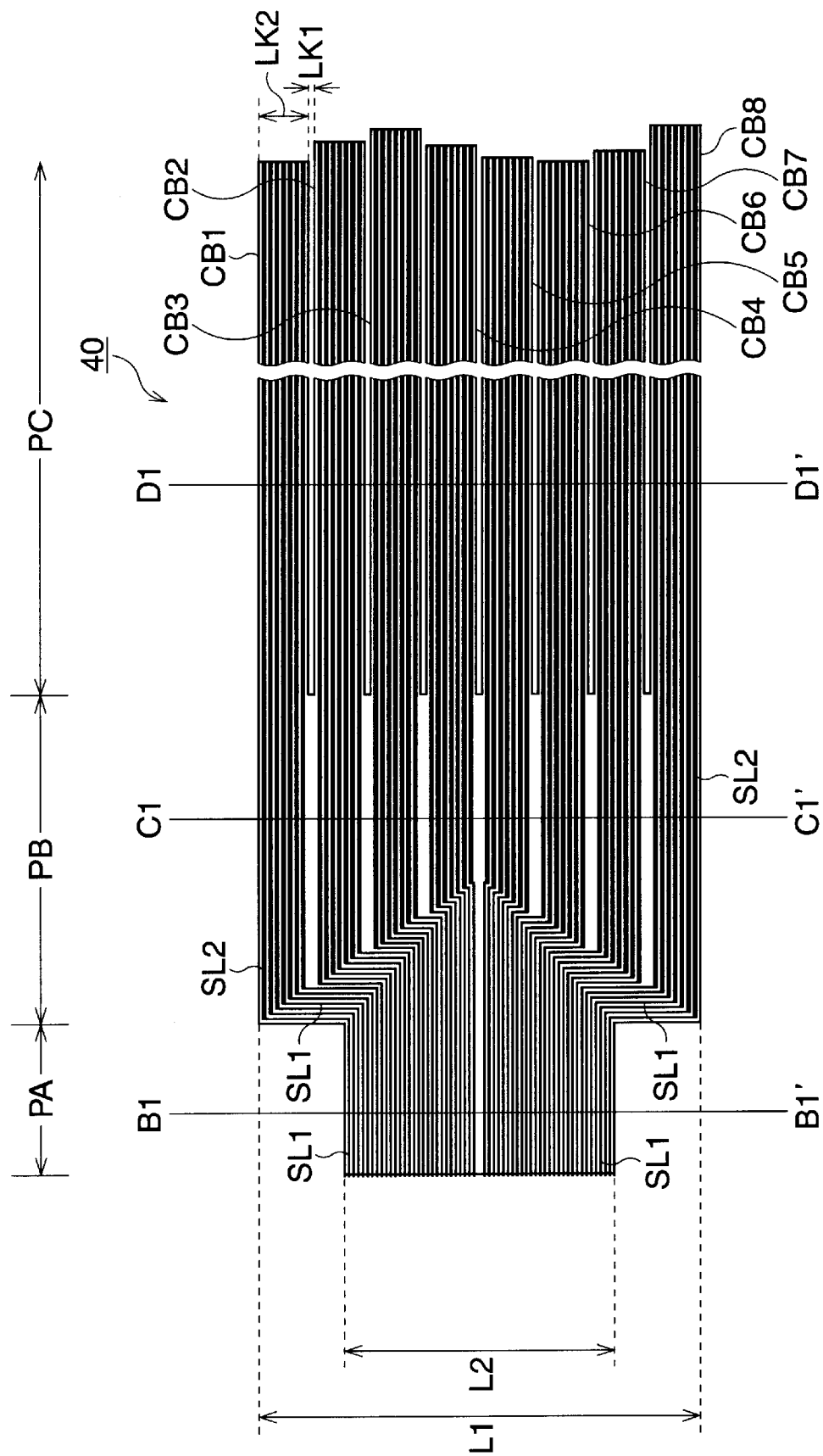
FIG. 8 is a view showing the unfolded flexible circuit board.

FIG. 7 is a schematic perspective view of the flexible circuit board formed in the endoscope 10. FIG. 8 is a view showing the unfolded flexible circuit board.

The flexible circuit board 40 is a flexible and thin substrate, which is formed by using a polyimide film or polyester film. The form of the flexible circuit board 40 can be arbitrarily set, namely, the flexible circuit board 40 can be formed to make any predetermined shape as required. In this embodiment, the flexible circuit board 40 is shaped like a "cone", as shown in FIG. 7. The circumferential line portion CL is connected to the arc-shaped ultrasonic wave sender-receiver 41 shown in FIG. 6. In the point-base portion 13, the flexible circuit board 40 is formed in a barrel. In the bending portion 12, the flexible circuit board 40 is constructed of a plurality of flexible circuit board strips. The plurality of flexible circuit board strips are connected to ultrasonic wave coaxial signal lines (herein not shown). The ultrasonic wave coaxial signal lines are bundled so as to form an ultrasonic wave coaxial cable (herein not shown) extending toward the manipulator portion 15. The circuit board strips extend along the central axis SD in the bending portion 12. Note that, in FIGS. 7 and 8, part of the plurality of circuit board strips is omitted, or not shown.

The cone-shaped flexible circuit board 40 is formed by rounding the flat and rectangular flexible circuit board 40' shown in FIG. 8. In FIG. 8, sections PA and PB correspond to the range of the point-base portion 13 and the ultrasonic probe 14. Section PC corresponds to the range of the bending portion 12. The width "L2" at the section PA, namely, the length of the circumference line portion CL, corresponds to the scanning range. The width "L1" at the sections PB and PC, greater than the width "L2", corresponds to a circumferential length of the point-base portion 13 and the bending portion 12. At the section PC, namely, corresponding to the range of the bending portion 12, the rectangular flexible circuit board 40' is divided into the eight strips. Each interval "LK1" between a circuit board strip and adjacent circuit board strip is equal and the width "LK2" of each circuit board strip is equal. Note that, the longitudinal length is different in each circuit board strips. Hereinafter, the eight circuit board strips are designated by "CB1, CB2, . . . , and CB8".

On the rectangular flexible circuit board 40', printed wirings, namely, conduct lines are formed. Printed wiring SL2, formed in the section PB and the section PC, is bolder than the printed wiring SL1 formed in the section PA. Note that, printed wiring is not shown in FIG. 7. The boldness of each signal line of the printed wiring SL2 depends upon the width "L1" and the width "LK2". The boldness of each signal line of the printed wiring SL1 depends upon the width "L2", namely, the scanning range.

Figure 9A:
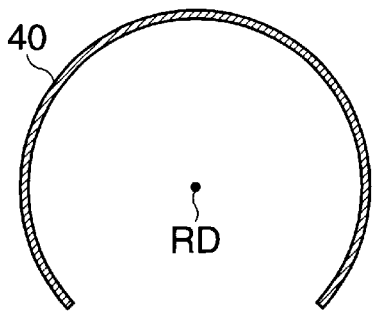
FIGS. 9A to 9C are section views of the flexible circuit board in the point-base portion and the bending portion.
Figure 9B:
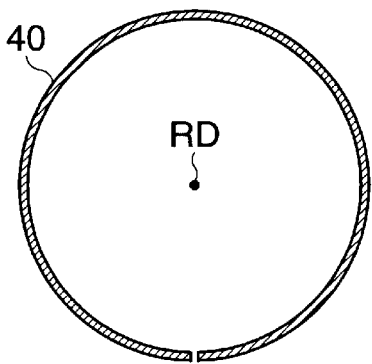
Figure 9C:
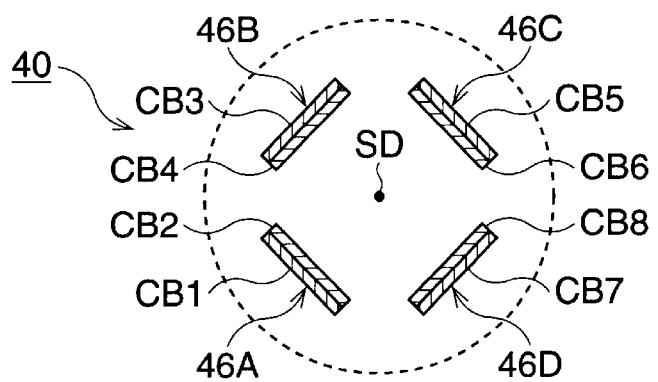

FIGS. 9A to 9C are section views of the flexible circuit board 40 in the point-base portion 13 and the bending portion 12. FIG. 9A is a section view at the line II–II', FIG. 9B is a section view at line III–III', and FIG. 9C is a section view at line IV–IV'. Note that, the lines II–II', III–III', IV–IV' are shown in FIGS. 3 and 7. The section view at the line II–II' is a section view in the point-base portion 13 and near to the ultrasonic probe 14. On the other hand, the section view at line III–III' is a section view in the point-base portion 13 and near to the bending portion 12. A section view at line IV–IV' is a section view in the bending portion 12. Lines B1–B1', C1–C1', D1–D1', shown in FIG. 8, correspond to the lines II–II', III–III', IV–IV', respectively.

As shown in FIG. 9A, the flexible circuit board 40 is formed in an arc, approximately 270 degrees, in accordance with the arc-shaped ultrasonic wave sender-receiver 41, namely, 20 the scanning range. On the other hand, the flexible circuit board 40 is formed in a circle at the line III–III' (See FIG. 9B). Then, as shown in FIG. 7 and FIG. 9C, a circuit board strip and an adjacent circuit board strip among the eight circuit board strips CB1 to CB8, are bundled so that they form four couples or bundles 46A, 46B, 46C, and 46D. The circuit board bundle 46A is composed of the two circuit board strips CB1 and CB2. Similarly, The circuit board bundles 46B, 46C and 46D are composed of the two circuit board strips CB3 and CB4, CB5 and CB6, CB7 and CB8, respectively. At the neighborhood of the flexible tube 11, the four circuit board bundles 46A to 46D are again separated into the eight circuit board strips CB1 to CB8.

FIG. 10 is a view schematically showing the ultrasonic wave coaxial signal lines and the ultrasonic wave coaxial cable in the endoscope.

The separated eight circuit board strips CB1 to CB8 are connected to loose, or unbundled signal lines 51 in the flexible tube 11. The signal lines 51 are composed of eight ultrasonic wave coaxial signal lines "SB1, SB2, . . . , and SB8", which are connected to the eight circuit board strips CB1, CB2, . . . , and CB8 respectively by precise soldering. Each of the cylindrical coaxial signal lines SB1 to SB8 is formed by copper wire, which is covered with insulator, such as polyvinyl chloride. The radius of each of the coaxial signal lines SB1 to SB8 is shorter than the width "LK2" of each of the circuit board strips CB1 to CB8. The ultrasonic wave coaxial cable 50 is formed by bundling the eight coaxial signal lines SB1 to SB8. The bundled eight coaxial signal lines SB1 to SB8 are covered with synthetic resin 50A. The synthetic resin 50A is an insulator. The ultrasonic wave coaxial cable 50 extends toward the second connector 80B.

The loose eight coaxial signal lines SB1 to SB8 are more flexible than the separated circuit board strips CB1 to CB8 and the ultrasonic wave coaxial cable 50, with respect to the compressing and extending forces. The forces operate against the circuit board strips CB1 to CB8, the eight ultrasonic wave coaxial signal lines SB1 to SB8, and the ultrasonic wave coaxial cable 50 along the central axis SD of the bending portion 12, and along the central axis PL of the flexible tube 11. When the compressing and extending forces occur because of the bending motion, the coaxial signal lines SB1 to SB8 are flexed and pulled, or extended as the coaxial signal lines SB1 to SB8 accept, or absorb the force. The coaxial lines SB1 to SB8 are durable against flexure, namely, snapping of the coaxial lines SB1 to SB8 does not occur by bending of the bending portion 12.

As shown in FIG. 10, the eight coaxial lines SB1 to SB8 are unbundled in the range LB2. The length of the range LB2, along the central axis PL, is substantially the same as the longitudinal length of bending portion 12 along the central axis SD, which is represented by "LB1" in FIG. 3.

Figure 11:
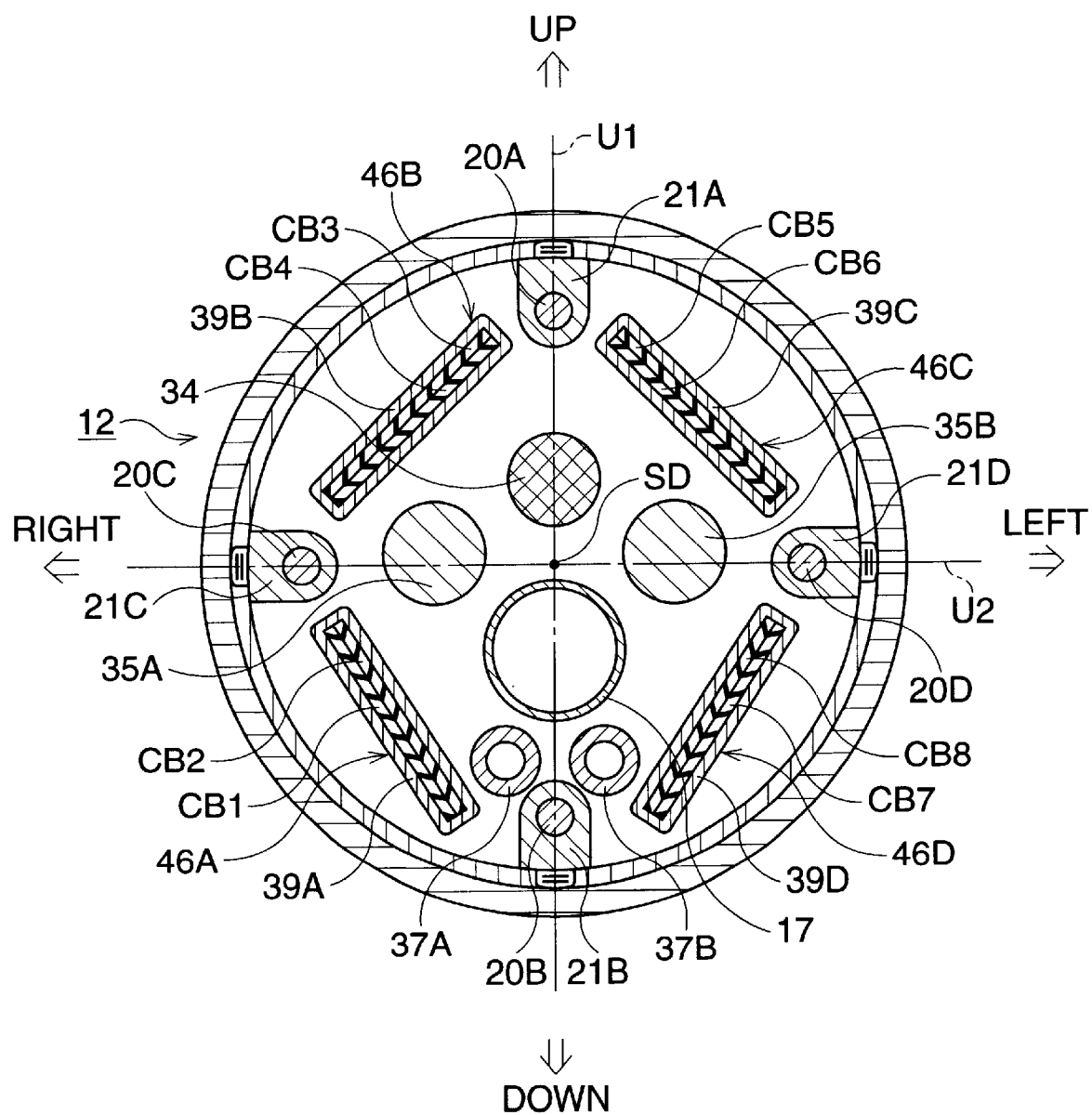
FIG. 11 is a section view of the bending portion, seen from the point side.

FIG. 11 is a section view of the bending portion 12, seen from the point side.

Wire guides 21A, 21B, 21C, 21D are provided between the manipulator portion 15 and the bending portion 12, and are arranged along the circumference of the flexible tube 11 and the bending portion 12, at intervals of 90 degrees.

The wire guides 21A and 21B are positioned along the up-down direction UD, and the wire guides 21C and 21D are positioned along the left-right direction. The wires 20A, 20B are installed in the wire guides 21A and 21B, respectively. Similarly, the wires 20C and 20D are installed in the wire guides 21C and 21D, respectively. The bending portion 12 bends toward the up or down direction by moving the wires 20A and 20B operatively connected to the up-down knob 16A, and bends toward the left or right direction by moving the wires 20C and 20D operatively connected to the left-right knob 16B. As shown in FIG. 11, in the bending portion 12, the forceps tube 17, image signal cable 34, the fiber-optic bundles 35A and 35B, and the delivery tubes 37A and 37B are provided.

The fiber-optic bundles 35A and 35B and the delivery tubes 37A and 37B are arranged so as to have symmetry with respect to a central line U1. Note that, the central line U1, defined in the section of the bending portion and crossing the central axis SD of the bending portion 12, corresponds to the up-down direction UD. The image signal cable 34 and the forceps tube 17 are arranged on the up-down central line U1 so as to have symmetry with respect to the central line U1. Note that, a left-right central line U2, defined in the section passing the central axis SD and perpendicular to the up-down central line U1, corresponds to the left-right direction.

As described above, in the bending portion 12, the flexible circuit board 40 is shaped in the four circuit board bundles 46A, 46B, 46C, and 46D. The circuit board bundle 46A is covered with a flexible heat shrinking tube 39A so that the circuit board bundle 46A and the heat shrinking tube 39A are unified. Similarly, the circuit board bundles 46B, 46C, and 46D are covered with heat shrinking tubes 39B, 39C, and 39D, respectively.

The circuit board bundles 46A, 46B, 46C, and 46D are arranged around the image signal cable 34, the fiber-optic bundles 35A and 35B, the delivery tubes 37A and 37B, and the forceps tubes 17, and are arranged generally along straight lines connecting the four wires 20A, 20B, 20C, and 20D. Therefore, the four circuit board bundles 46A, 46B, 46C, and 46D are at an angle of an generally 45 degrees to the up-down central line U1, and are not arranged on the central line U1. Further, the four circuit board bundles 46A, 46B, 46C, 46D are arranged so as to have symmetry with respect to the up-down central line U1 and the left-right central line U2.

In the bending portion 12, powder lubricants, such as a molybdenum disulfide, are filled. Therefore, the positions of the four circuit board bundles 46A, 46B, 46C, 46D, the image signal cable 34, the fiber-optic bundles 35A and 35B, the delivery tubes 37A and 37B and the forceps tube 17 do not substantially change while moving the bending portion 12.

In this way, in this embodiment, the ultrasonic wave sender-receiver 41 is formed along the circumference of the ultrasonic probe 14, namely, the plurality of ultrasonic wave vibratos are arranged along the circumference. The ultrasonic waves are sent radially around the central axis of the point RD for performing the electronic radial scanning. Further, the flexible circuit board 40 is provided for transmitting the signals associated with the ultrasonic waves and echoes. In the bending portion 12, the flexible circuit board 40 is constructed of the eight circuit board strips CB1 to CB8, and unified in the four circuit board bundles 46A, 46B, 46C, and 46D.

The eight circuit board strips CB1 to CB8 are connected to the eight ultrasonic wave coaxial signal lines SB1 to SB8 respectively in the flexible tube 11. The eight coaxial signal lines SB1 to SB8 are loose in the range LB2, and are bundled such that the coaxial cable 50 is formed except for the range LB2. While manipulating the bending portion 12, the loose coaxial signal lines SB1 to SB8 are flexed and extended when the compressing and extending forces occur along the central axes PL and SD. Namely, the unbundled coaxial lines SB1 to SB8 absorb the compressing and expanding forces by flexure and extending. Thus, the circuit board strips CB1 to CB8 are not folded along the central axes PL and SD. Namely, excessive flex and extension do not occur in the circuit board strips CB1 to C8 while moving the bending portion 12 and therefore snapping of the printed wiring on the circuit board strips CB1 to CB8 does not occur.

In the above embodiment, the eight circuit board strips CB1 to CB8 are formed by partially cutting the single rectangular flexible circuit board 40'. However, the flexible circuit board 40' may be partially cut such that the number of circuit board strips is a number other than eight (for example, twelve). Further, in place of utilizing a partially-cut flexible circuit board 40', the flexible circuit board 40 may be composed of a plurality of circuit board strips. In this case, each of the strip-shaped circuit board strips is connected to the ultrasonic wave sender-receiver 41. The thickness and width of each circuit board strips may be defined in accordance with the radius of the bending portion.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Application No. 2000-353745 (filed on Nov. 21, 2000) which is expressly incorporated herein, by reference, in its entirety.

What is claimed is:

1. An ultrasonic endoscope comprising:
    a bending portion in a tube and connected to a flexible tube insertable into a body, said bending portion being bent by remote control;
    an ultrasonic probe operatively connected to said bending portion and comprising a plurality of ultrasonic wave vibrators arranged circumferentially, said plurality of ultrasonic wave vibrators sending ultrasonic waves radially and receiving echoes of the ultrasonic waves;
    a flexible circuit board that transmits ultrasonic wave signals associated with the ultrasonic waves and the echoes, said flexible circuit board comprising a plurality of flexible circuit board strips in said bending portion so as to allow a bending motion, said plurality of flexible circuit board strips extending along a first central axis of said bending portion; and
    an ultrasonic wave coaxial cable that is provided in said flexible tube and comprising a plurality of ultrasonic wave coaxial signal lines, each of said plurality of ultrasonic wave coaxial signal lines being separate and extending from said ultrasonic wave coaxial cable along a second central axis of said flexible tube and being connected to said plurality of flexible circuit board strips,
    wherein said plurality of ultrasonic wave coaxial signal lines are more flexible than the plurality of circuit board strips so as to absorb compressing and extending forces, which act along the first and second central axes, against said plurality of flexible circuit board strips, against said plurality of ultrasonic wave coaxial signal lines, and against said ultrasonic wave coaxial cable.

2. The ultrasonic endoscope of claim 1, wherein a lengthalong the central axis of said flexible tube is at least equal to a length of said plurality of flexible circuit board strips along the first central axis of said bending portion.

3. The ultrasonic endoscope of claim 1, wherein said flexible circuit board comprises a single rectangular flexible circuit board having an arcuate shape, said plurality of flexible circuit board strips being defined by slits in said flexible circuit board.

* * * * *